(12) United States Patent
Lu et al.

(10) Patent No.: US 6,203,757 B1
(45) Date of Patent: Mar. 20, 2001

(54) FLUID SAMPLE DISTRIUTION SYSTEM FOR TEST DEVICE (75) Inventors: Frank Lu, San Mateo; Liang Chan, San Bruno, both of CA (US)

(73) Assignee: Bionike, Inc., S. San Francisco, CA (US)

( * ) Notice: Subject to any disclaimer, the term of this patent is extended or adjusted under 35 U.S.C. 154(b) by 0 days.

(21) Appl. No.: 09/204,398

(22) Filed: Dec. 2, 1998

(51) Int. Cl.$^7$ .................................................. G01N 33/48
(52) U.S. Cl. ............................ 422/58; 422/61; 436/815; 436/901
(58) Field of Search ...................... 422/58, 61; 436/164, 436/169, 815–816, 901

(56) References Cited

U.S. PATENT DOCUMENTS

| | | | |
|---|---|---|---|
| 3,915,639 | * 10/1975 | Friedenberg | 422/58 |
| 5,141,875 | * 8/1992 | Kelton et al. | 422/56 |
| 5,270,166 | * 12/1993 | Parsons et al. | 435/7.4 |
| 5,556,789 | * 9/1996 | Goerlach-Graw et al. | 436/169 |
| 5,916,815 | * 6/1999 | Lappe | 436/92 |
| 5,976,895 | * 11/1999 | Chipowski | 436/518 |

* cited by examiner

Primary Examiner—Lyle A. Alexander (57) ABSTRACT

Diagnostic products having multiple test strips within a unitary diagnostic test device, or test icon, are described herein. In the preferred embodiments of the diagnostic test device of this invention, a fluid sample distribution system is provided wherein a sample collection and distribution port is provided in the housing for receipt of a biologic fluid sample and the channeling of such sample onto a sample receiving web. The sample receiving web, which is located within the test device, is in fluid communication with an array of test strips, and is configured to deliver an aliquot of biologic fluid sample to the test site of each such test strip at essentially the same rate. In the preferred embodiments of this invention, the sample receiving web comprises at least one base segment and at least one branched segment. Each of the base and branched segments can be formed or cut from a common sheet of material or from separate sheet material and thereafter placed in contiguous relationship one another. The relative placement of the sample receiving web within the test device is coincident with a portion of each test strip and designed to effect the balanced distribution and delivery of an aliquot of the biologic fluid sample to the test site of each of the test strips within the test device.

19 Claims, 4 Drawing Sheets

FLUID SAMPLE DISTRIUTION SYSTEM FOR TEST DEVICE

BACKGROUND OF THE INVENTION

1. Field of the Invention

This invention is directed to a fluid sample distribution system for a test device. More specifically, this invention relates to a system and device for concurrent performance of multiple discrete analysis on a common test fluid by the passive and balanced distribution of the test fluid to the discrete test strips within the device.

2. Description of the Prior Art

The increasing popularity of simple and rapid diagnostic test kits for self-testing, and for use in professional environments devoid of elaborate instrumentation for sample preparation and analysis, has become increasingly prevalent because of the accuracy and relatively modest costs involved in the use of such products. Generally all of these products share the following common components, test format and performance criteria:

(a) a porous or bibulous medium for receipt of the sample, (which may also provide a source of test kit reagent for analysis of the sample), (b) a test strip specific for detection of an analyte of interest, (c) one or more test kit reagent(s) within the test strip that is (are) immobilized at a test site, (d) interaction of the sample with a test kit reagent in the test strip so as to produce a discernible physical change (e.g. color) at the test site of the test strip, (e) the ability to accommodate a relative substantial volume of sample (in comparison to automated/ instrument based test systems), (f) manipulation of the sample to effect separation of endogenous sample constituents and unreacted test kit reagents at the test site, so as to produce a clean reaction product in the test site.

In a number of instances the methodology for performance of the such user oriented self-testing contemplates the application of a minimum volume (generally a substantial excess) of sample to the test device, so as to reconstitute the pre-disposed test kit reagents and thereby effect their interaction with the constituents of the sample. In order to effectively isolate the reaction products of such interaction within the test strip, either the analyte from the sample, or the reaction product of an analyte and a test kit reagent, become immobilized at a test site within the test strip, so as to cause a discernible physical change. For example, in the performance of a simple test for the detection of a drug of abuse, a test strip is provided with an immobilized binding substance that is specific for interaction with an epitope of the analyte of interest or a metabolite of the analyte of interest. Upon application of the sample to the sample collection web, the sample suspected of containing the analyte of interest, (e.g. cannabinoid compounds, where the test is specific for Marijuana), reconstitutes the test kit reagents in the sample collection web, (e.g. colloidal sold conjugated to an antibody specific for the analyze), and thereupon interacts with such test kit reagents to form an immunocomplex between the conjugate and analyte. This immunocomplex further reacts with the immobilized binding substance which migrates along the fluid pathway of the test strip to the test site within the test strip. As the immunocomplex becomes increasingly concentrated by the immobilized binding substance at the test site, a visible color, characteristic of the gold labeled immunocomplex appears. The appearance of this visible color is both time dependant and dependant upon the concentration of the analyte in the sample. More specifically, color development at the test site requires the concentration of the immunocomplex at the test site until the optical density thereof is sufficient to become visible to the naked eye—the so-called "direct indicator" of the presence of the analyte of interest.

In this type of assay, the volume of sample must be sufficient to provide sufficient analyte to produce the requisite concentration of immunocomplex necessary for visible color formation. This visualization of the immunocomplex is also (indirectly) dependent upon the absence of endogenous sample components at the test site which can interfere in such color development. Accordingly, such tests generally specify an amount of sample that can both satisfy the kinetics of the assay chemistry and, in addition, insure the requisite clean separation of the endogenous sample components from the immunocomplex at the test site. This clean separation can be more critical where, for example, the analyte is only present in very minute quantities, or where the test is biased to differentiate an elevated level of analyte from a basal level of analyte (e.g. analysis for HCG in pregnancy tests) within the fluid sample.

Historically, the performance of multiple analysis of a common test sample has generally required the use of automated instrumentation (Technicon SMAC Analyzer; Dupont ACA Analyzer; Baxter Healthcare PARAMAX Analyzer, and the like). This so-called "profile" analysis of a common test sample has also been postulated as capable for performance on a manual test device, however, it is believed that no such product has even been successfully produced, marketed and/or sold.

The ability to manipulate multiple samples, and/or perform multiple analysis within a common test device has, however, been described in the literature for use in conjunction with various assay formats, such as radioimmunoassay (RIA), fluorescence immunoassay (FIA) and enzyme immunoassay (EIA or ELIASA), U.S. Pat. No. 5,141,875 (to Kelton et at, issued Aug. 25, 1992). According to Kelton concurrent, multiple analysis of a common test fluid can be performed by "conjunctive centrifugation and wicking induced flow" of a sample by the dispensing individual aliquots of sample onto discrete areas of a sample receiving web within a rotary fluid manipulator of the type illustrated in his patent; and, thereafter applying an eluent to a common, centrally located reservoir, wherein such eluent flows from such common reservoir into each discrete fluid pathway and so as to cause the individual samples, in each discrete pathway, to migrate to a binding antigen specific for its detection and/or for further interaction with a companion reagent. As above noted, the label used in this analysis for the manifestation of the presence of the analyte of interest can be any of the common indicators, depending upon the assay protocol (FIA, RIA, ELISA).

Other patents and product literature showing manipulation of common test fluids within various test devices for performance of multiple analysis are well-known in the prior art, and typically include test formats analogous to chromatography, wherein a series of discrete and separate samples are spotted on a common the test medium, cross-migration therebetween inhibited by either physical isolation thereof or modification of the medium, or other common expedients, and a fluid carrier (generally containing a test kit reagent) applied to the medium to effect interaction of the sample and the test kit reagents.

As is evident from the foregoing discussion, there is and remains a continuing need for the development of an integral system for profile analysis of a common test sample to accommodate the needs of the self-testing environment of the individual, and of the professional testing environments lacking elaborate instrumentation. In order to be acceptable for use in either of these environments, the device and test protocol need be both compact and have the ability to distribute and contain a relative large volume of sample (which in a number of test situations) may include a highly infectious sample. In addition, the appropriate testing device need have the ability to conduct the prescribed panel of tests at essentially the same time, or concurrently, so as to afford availability of the test results for each of the assays within a precise time frame. Lastly, the successful test device design must be economic to produce so as to contain the cost of such test device to permit its availability to the broadest market for such kits. With respect to latter requirement, the achievement of this goal necessarily requires the ability to adapt existing test strips and test protocols to such a multiple assay delivery system. As is apparent from a review of the marketplace, the competitive product literature and the technical (patent) literature, no such device has as yet been suggested which can meet each of the above objectives. So long as this need continues, the consumer will be required to continue to purchase several different products to perform discrete assays to obtain comprehensive analysis of a single test sample for the information essential to monitor and/or diagnose body fluid constituents, which are essential to confirm a healthy condition and/or to diagnose a disease states.

OBJECTS OF THE INVENTION

It is the object of this invention to remedy the above as well as related deficiencies in the prior art.

More specifically, it is the principle object of this invention to provide a test device for performance of concurrent multiple analysis of a common test fluid for a number of discrete analytes.

It is another object of this invention to provide a manual system for the essentially uniform distribution of a common test fluid along a plurality of discrete test strips within a common test device.

It is yet another object of this invention to provide a manual system for the essentially concurrent analysis of common test fluid for a plurality of discrete analytes within a common test device.

It is still yet another object of this invention to provide a manual system for performance of a panel of tests on a common test fluid through the passive manipulation and distribution of a test fluid within a test device, so as to effect the balanced flow of such test fluid to a plurality of discrete test sites for essentially simultaneous detection of discrete analytes that are believed to present in the test fluid.

Additional objects of this invention include the provision of a multi-strip test device for performance of a profile analysis of a common biologic fluid sample for drugs of abuse.

SUMMARY OF THE INVENTION

The above and related objects are achieved by providing a fluid transfer system and test device incorporating such fluid transfer system for essentially uniform distribution of a test fluid to an array of test strips from a common fluid source/reservoir within the test device. In one of the preferred embodiments of this invention, the test device comprises a housing having a chamber defined by two essentially planar components, specifically, a face plate and base member, that when assembled form a unitary structure. The housing is intended for receipt of a test fluid (e.g. biologic fluid sample such blood, urine or saliva) and the delivery thereof onto a sample receiving web (e.g. fiberglass) for essentially passive manipulation and distribution of a test fluid to several discrete test strips within the test device. Each of the test strips contained with the chamber are maintained in fluid communication with the sample receiving web and yet isolated from one another. The test strips utilized in the test device of this invention typically contain test kit reagents that are specific for the detection of an analyte of interest that is believed to be present in the test fluid. In the preferred embodiments of this invention, a face plate of the housing is provided with a sample receiving port and one or more windows for viewing the test results for each test strip which may be contained therein. Each of the face plate and base member of the housing are preferably further internally modified to provide a series of guides or channels for proper orientation of each of these internal components relative to one another, and for placement and orientation of the sample receiving web and test strips which are contained therein. In the preferred embodiments of this invention, the sample is delivered through the sample receiving port (e.g. opening or hole) located at one end of the face plate of the housing and, thereafter, dispensed/directed onto the sample receiving web so as to be effectively drawn into the test device where it is rapidly absorbed by the sample receiving web. Where, as in the preferred embodiments of this invention, the device is designed to contain at least two (2) test strips, and most preferably in excess of two (2) test strips, the volume of test fluid required to perform three discrete analysis can be considerable.

Because of the substantial volume contemplated for application to the diagnostic test device, the manner of distribution of the fluid sample, and possibly addition of a companion reagents to each of the test strips, the manipulation of the fluids delivered to this test device must be modulated/balanced by the sample receiving web. This balance is accomplished within the test device by the concurrent distribution of the fluid sample to at least two spaced apart location on each test strip which are upstream from the test site. More specifically, the configuration of the sample receiving web affords the concurrent distribution of an aliquot of sample fluid to the end of each test strip and an aliquot of sample fluid to a portion of the test strip located between the end of the test strip and the test site of the test strip. This essentially concurrent distribution of multiple aliquots of a fluid sample to a given test strip is accomplished with a sample distribution web having a tree-like structure, specifically a trunk or base that is normal (at right angles) to the end of the test strips, and a series of branches that radiate from this base and which contact the test strips at an acute angle relative to the base.

It is further emphasized that the delivery of an aliquot of test fluid to each test strip by a given branch of the sample receiving web is to a different location on each test strip within the test device, depending upon its relative position within the housing; and, that as the fluid is absorbed into each of the test strips at each of those two separate locations, the apparent volume of fluid within each test strip becomes essentially balanced, so as to cause such fluid to contact the test site of each test strip at essentially the same point in time. This passive manipulation and distribution of the fluid sample to multiple test strips afford essentially concurrent (simultaneous) performance of a panel of assays on a common sample within a simple and unitary test environment.

In the preferred embodiments of this invention, each of the test strips within the test device is specific for a discrete (different) analysis that is believed to be present in the test fluid. The size, placement and orientation of the sample receiving web relative to the individual test strips effects essentially uniform distribution of test fluid, the unique ability to accommodate sufficient volume of sample to perform a panel of assays with a common fluid sample and, the concurrent analysis of a common fluid sample for several discrete analytes. As shall be described herein in greater detail, the passive and balanced distribution of the test sample afforded by the system of this invention utilizes multiple fluid pathways from the sample receiving web to each of the test strips, to overcome and compensate for the disparity in the relative distance between the point of application of the sample onto the sample receiving web and tile junction of the fluid communication/transfer of fluid from the web to each of the test strips within the test device.

DETAILED DESCRIPTION OF THE INVENTION INCLUDING PREFERRED EMBODIMENTS

The device of this invention as illustrated in the foregoing Figures includes a number of elements in common and, thus, for the purpose of ease of understanding each of these common elements are referenced with a common numeral or designation.

Figure 1:
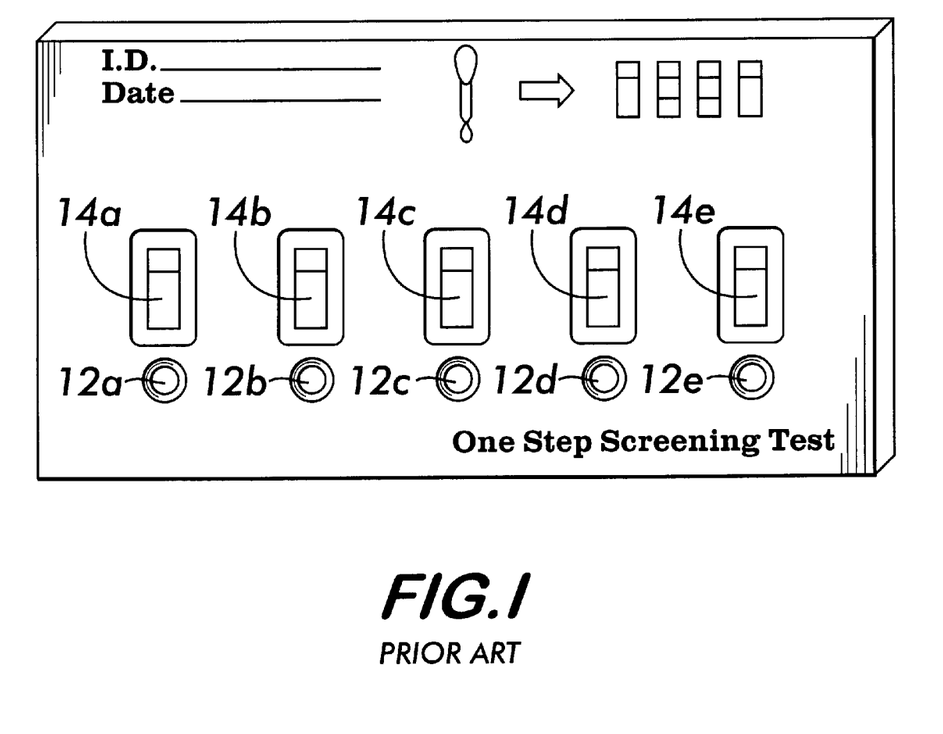
FIG. 1 is a perspective view of a diagnostic test device representative of the prior art.

FIG. 1 is typical of the prior art and is illustrated herein for purposes of comparison to the structure, function and operation of the device and system of the instant invention. More specifically, the prior art device illustrated in FIG. 1 includes a series of discrete sample application/receiving site (12) that directs the uptake and distribution of an aliquot of the sample (13) to each of the individual test strips (14). As is evident from the placement of the test strips in this device, the sample is distributed by a wicking and/or capillary action from the discrete sample application/receiving, site (12) to the test site and, thereafter, the results observed by monitoring for perceptible changes in the viewing window. In addition, this device can include a number of modifications to accommodate consumer oriented features, such as color comparator and graphic information directing the manner in which the test is to be performed and/or how the results of such test are to be interpreted.

By way comparison, in one or the preferred embodiments of the invention shown in FIGS. 2, 2A, 2B & 2C, the system of this invention illustrates the adaptation of an array of conventional test strips (24) to a multiple test device (20) that permits effective and concurrent testing of a common sample for a plurality of analytes within a given (essentially the same) time frame.

This latter feature and advantage is both significant and, in the case of certain tests can be critical, where the test results for a given assay may indicate a negative result when the test site is viewed at the prescribed interval, and a false positive result if viewed after the period in which the test results are to be read. Thus, any inordinate delay in the concurrent performance of the complete panel of tests, can result in inaccurate reporting, of one or more of the results of the panel where there is delay in the development of only one the tests or test indicators.

Figures 2, 2A, 2B:
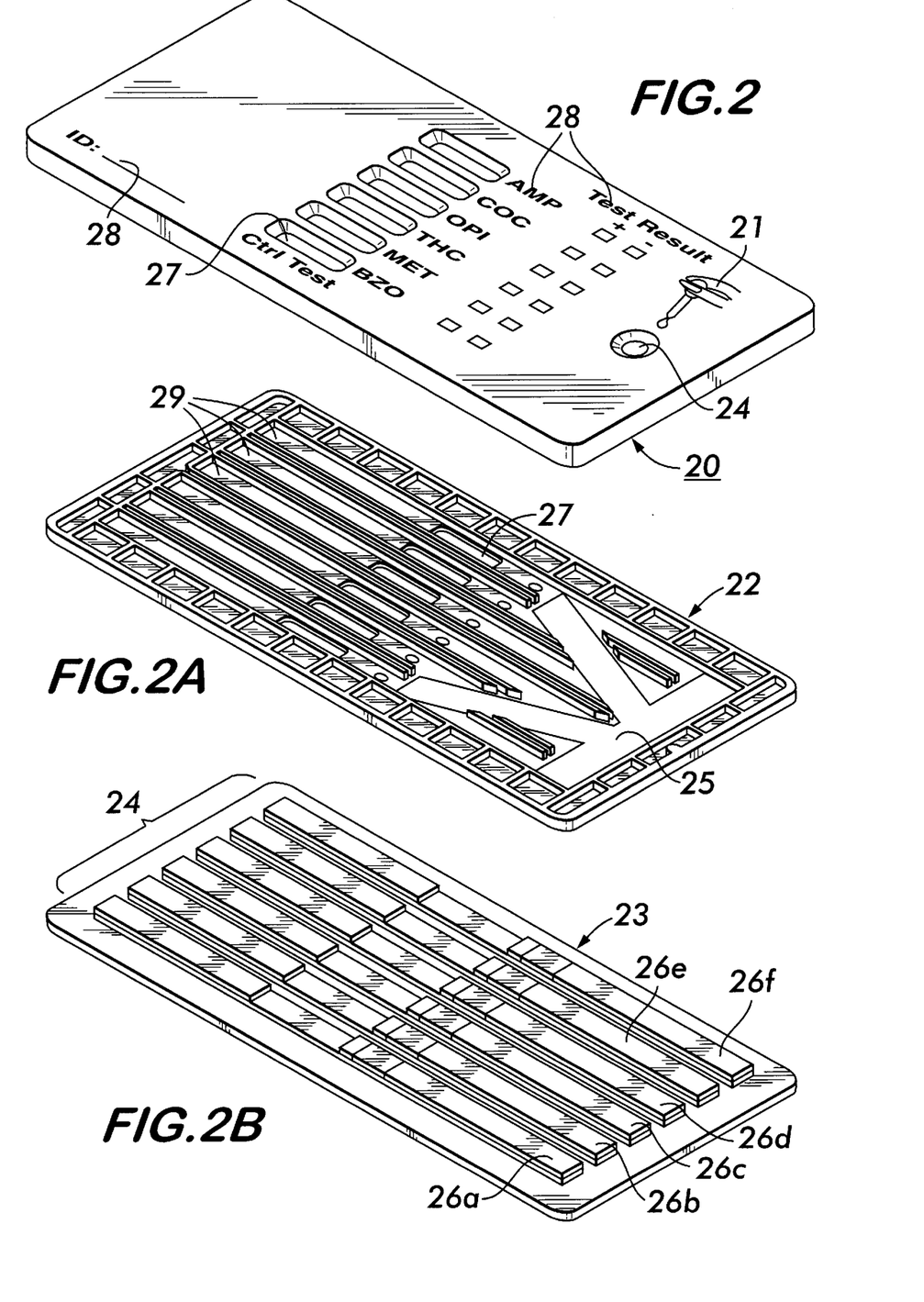
FIG. 2 is perspective view of a test device of this invention.
FIGS. 2A & 2B provide a perspective view of the interior components of the housing of the test device of FIG. 2.
Figure 3:
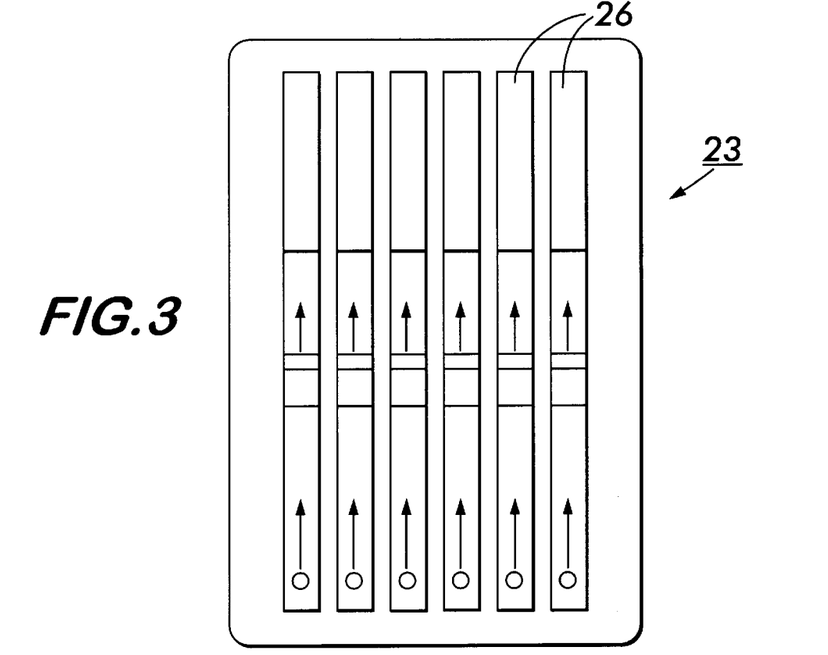
FIG. 3 illustrates an array of test strips within a test device of the type depicted in FIG. 2.
Figure 4:
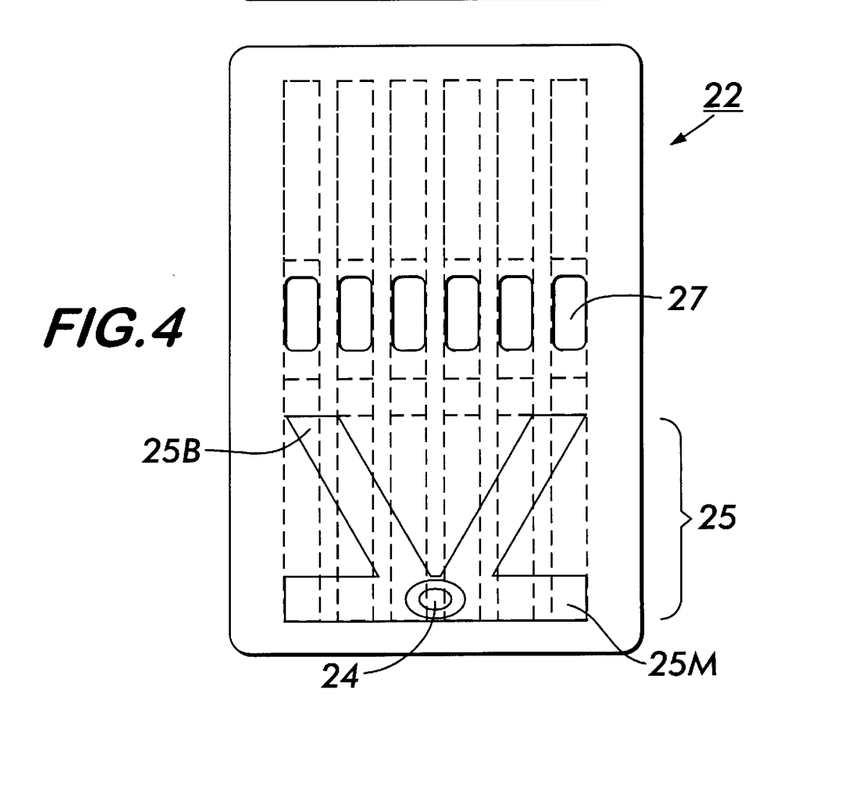
FIG. 4 is diagrammatic illustration of a fluid distribution system within a test device of the type depicted in FIG. 2.
Figure 5:
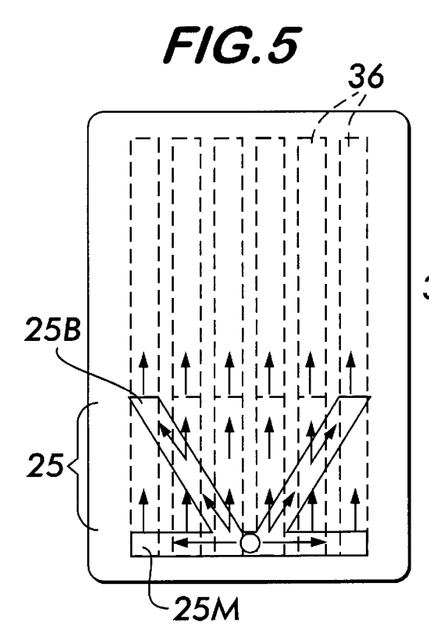
FIG. 5 is diagrammatic illustration of the fluid distribution pathway for a diagnostic test device of this invention wherein the contemplated analysis has six (6) discrete diagnostic test strips.

The individual components of the device of FIG. 2 comprise a housing (21) having at least two interlocking components, a face plate (22) and a base (23). FIGS. 2A & 2B depict an exploded view of the housing of FIG. 2, including specifically, the molded-in features that provide the template for the placement and isolation of the array of test strips and sample distribution web within the device. FIG. 2B depicts the array of test strips and their relative arrangement vis-a-vis the internal components of this device are illustrated in FIG. 2. FIG. 2A depicts the functional arrangement of the internal components of the test device relative to the functional features of the face plate.

As illustrate in FIGS. 2 & 2A, the face plate (22) includes a port or hole (24) which is formed at one end of the device and coincides with an internally positioned sample receiving/distribution web (25) and, also possibly one of the test strips (26a-e) associated with the test device. This web (25), which is described in greater detail hereinafter in the discussion of FIGS. 4 to 7, inclusive, can comprise a naturally occurring material, such as cellulose, or a synthetic (such as fiberglass, nitrocellulose or polysufone) having a substantial void volume (porosity) to accommodate the anticipated delivery of sufficient fluid to perform numerous tests. The fact plate (22) also contains a number of viewing windows (27) to permit access to and observation of visual changes caused to test strips by interaction with the fluid sample. The viewing windows (27) are generally parallel to one another as illustrated in FIGS. 2 & 2A, and their relative orientation is relative to one another and the sample receiving/distribution web is discussed in detail hereinafter. Additional functional features of the face plate (22) will typically include graphic infomiation (28) directing the user as to where to apply the sample, and the location for viewing or reading the result of the test. Additionally, the ideiitity of the analyte for each of the test strips is typically referenced on the face plate in order to differentiate the analyte results for a given test. In addition, it may be advantageous to include a color chart or comparator (not shown) on the face plate to provide semi-quantitative measurement of the analyte of interest. This latter feature may be desirable, for example, to monitor therapeutic drug levels to insure that the drug is maintained at a therapeutic level, as is essential, for example, in the monitoring of the therapeutic range of anti-convulsants. hi addition, indicia (not shown) may also be present to direct the tester in the safe and effective disposal of the test device, as in the case of testing for infectious disease (HIV, Hepatitis, Mononucleosis, etc.).

The second major component of the housing is depicted in FIG. 2B, and comprises a base member (23) that is designed to complement and interlock with the face plate (22), so that when these two components are assembled, the assembled device (20) defines a housing (21) having an internal chamber for positioning and containment of the sample receiving/distribution web (25) and test strips (26) relative to one another, and the functional features in the face plate (sample port and viewing windows) discussed hereinabove. In the preferred embodiments of the device illustrated in FIGS. 2 & 2B, each of the base member (22) and the face plate (21) also has a predefined series of pre-formed or molded parallel channels (29) for receipt and alignment of the tests strips (26a–e) within the housing so as to simplify manufacture and assembly. In the preferred embodiments of this invention illustrated in FIGS. 2, 2A & 2B, at least some of the molded-in features (e.g. channels) in the base member complementary and interlock with features that are molded into the interior surface of the face plate (23).

As depicted in FIGS. 4 to 7, inclusive, the sample receiving/distribution web (25) contained within the chamber of the housing comprise a segment (25N) which is at right angles to the orientation of the alignment of the test strips (26) within the housing (hereinafter referred to a the "base" or "normal" segment); and, at least two branched segments (25B), which are in fluid communication with the normal segment (25N) and, preferably coincident with the opening or port (in the face plate for receipt and distribution of the fluid sample. The location and angle of the branched segments (25B) relative to the normal segment (25N) of the web is dictated by the number of test strips within the device, the amount of sample needed to perform the desired test, the fluid absorption capacity of the web and of the individual test strips and possibly other factor of lesser (non-critical) importance.

Figure 6:
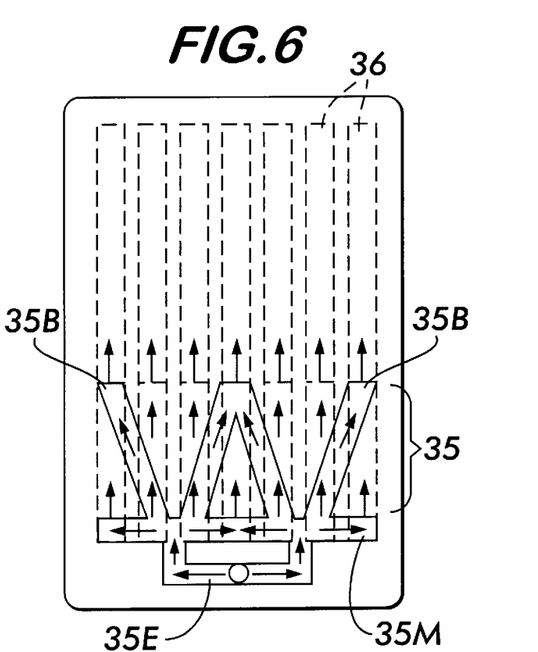
FIG. 6 is diagrammatic illustration of the fluid distribution pathway for a diagnostic test device of this invention wherein the contemplated analysis has seven (7) discrete diagnostic test strips.
Figure 7:
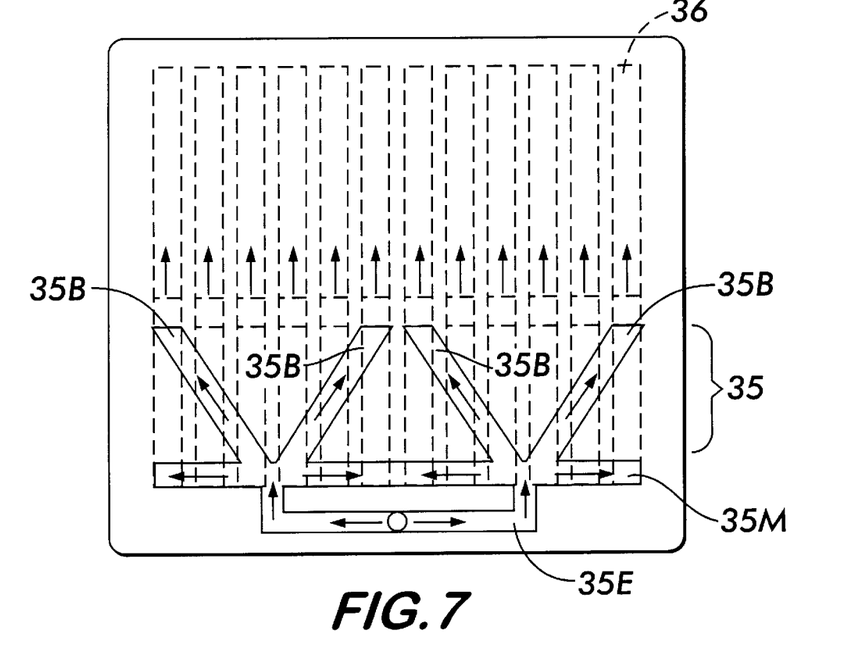
FIG. 7 is diagrammatic illustration of the fluid distribution pathway for a diagnostic test device of this invention wherein the contemplated analysis has twelve (12) discrete diagnostic test strips.

In FIGS. 6 & 7, an alternative web arrangement is depicted for effective sample distribution of sample for performance of seven (7) to twelve (12) concurrent assays on test strips (36). More specifically, FIGS. 6 & 7 depict the use a compound or multiple branch web (35) wherein each pair of branches (35B) are in fluid communication, with a common normal web segment (35N) located on one end of the test device. The normal segment (35N) of the common web is, as illustrated in FIG. 2C, in contact with each of the test strips (36) on one end thereof. In the embodiment of the invention illustrated in FIGS. 5, 6 & 7, the sample is dispensed through the sample collection/distribution port (not shown) in the face plate of the housing (in the same manner as discussed above in reference to FIGS. 4 & 5) onto a separate segment or extension (35E) of the normal segment (35N) of the web, and thereupon flows to the normal segment (35N) of the web where it is applied thereto at two spaced apart locations (37, 38) for further distribution to each of the multiple branched segments (35B) thereof. It is noted that extension (35E) of the normal segment (35N) of the web is configured to insure more uniform fluid sample distribution than is permissible from a single point of fluid application and, thus, essentially concurrent performance of the panel of tests within die test device. In order to rapidly absorb the requisite volume of test fluid within the test device, and thereafter effectively and uniformly distribute it among the individual test strips, the sample receiving web must be relative more porous than the test strips and/or have a substantially greater fluid capacity than such test strips to allow for the absorption of sufficient sample fluid within an abbreviated period; which period is invariably less than the period in which such sample could be directly distributed to each of the test strips within the test device.

As above described in the accompanying text and Figures, the sample receiving web (25, 35) is configured to effect absorption and distribution of the sample along at least three separate and discrete fluid pathways, with the further caveat that at least two of such pathways are maintained in concurrent fluid communication with each test strip at all times. It is further noteworthy and surprising, that the unique configuration of the web, in each instance, is effective to balance the absorption and flow of the sample among the several test strips of the device, notwithstanding that the introduction of sample into the housing of the test device is essentially coincident with the location of one end of one of the test strips, and the other test strips are at varying distances from this point of introduction of fluid into the housing. It is, of course, understood that the dynamics of fluid distribution of this invention is inclusive of a system and device in which one of the test strips is coincident with the plane of introduction of the sample into the housing, and that at such location, each of the base or normal segment (25N, 35N) of the web and at least one branch (25B, 35B) of the web appear to meet. More specifically, this test strip also benefits from a plurality of fluid pathways, with the caveat the fluid from each of these web components is applied juxtaposition to one anther on this test strip. More specifically, as the fluid in introduced into the device, the test strip coincident with the plane of fluid introduction cannot absorb sufficient fluid to perform the contemplated assay within the very abbreviated interval involved in fluid introduction. Thus, as fluid flow into the web, the volume applied at this juncture simply overwhelms the capacity of this test strip to absorb it. Accordingly, fluid flows away from this test strip into the web (25N, 25B) (35N, 35B) and, thereafter, is drawn back to this test strip upon equilibration of the volume absorption capacity of each of the test strips of the test device, Accordingly, this ebb and flow of sample to and from this test strip occurs in essentially the same manner as with respect to the other test strips, specifically the sample is applied to the test strip at two locations on the test strip (between the end of the strip and the test site), except that the two locations are just much closer together.

In the preferred embodiments of the system and device of this invention, the angle of a branch (25B, 35B) of tile sample receiving web (25, 35) relative to the base segment (25N, 35N) of the such web is preferably about 45 degrees; and most preferably greater than about 45 degrees and, the angle of contact of base segment (25N, 35N) of the such web relative to the end of each test strip (26, 36), is preferably about 90 degrees. In each instance, fluid is concurrently delivered from the sample receiving web (25N, 25B), (35N, 35B) to each test strip at two separate locations, to effect essentially uniform distribution along the test strip relative to the test site for each strip.

The test protocols suitable for use in the multiple test environment of the system and device of this invention can include any of the common test protocols presently available for testing of a sample acquired by non-invasive means (e.g. urine and saliva) and samples acquired in by more invasive techniques (e.g. blood and serum). As is evident from the above discussion, sufficient sample volume must be available to effect the requisite distribution within the test device. Where the acquired sample volume is less than the that preferred for use in this device, the sample can be pre-diluted with buffer or other suitable diluent, and, thereafter applied, Alternatively, where the sample is applied to the web at insufficient volume, an eluent can be coincidentally applied to the web to effect its distribution within the device. Moreover, the test device of this invention also contemplates, in addition to sample, the application of any fluid that is common to all of the discrete assays. For example, where the test protocol selected for the strips of the device is an enzyme immunoassay, and the indicator is the same enzyme for each enzyme labeled immunoreagent, it is contemplated that a common substrate solution be applied to the sample collection web, in the same manner as the sample, to afford visualization of test results for each of the discrete assays.

In one of the preferred embodiments of this invention, it is contemplated that a given device include a panel of related assays, e.g., a drug panel (cocaine, amphetamines, etc.), infectious disease panel (hepatitis, HIV, Mononucleosis), or a fertility panel (HCG, LH, etc,), and the like. It is further understood that the configuration of the test device as illustrated herein in but one of number of the potential embodiments of the passive fluid manipulation and distribution system of this invention; and, the absence of description of such alternatives is not intended as limiting the scope of this invention which has been reserved for the following claims.

What is claimed is:

1. In a test device for concurrent analysis of a sample for multiple analytes on multiple test strips within said test device, wherein said test device has (a) a plurality of test strips specific for detection of distinct analytes, and (b) a common sample application site in fluid communication with each of said test strips within said test device, the improvement comprising:

a test device having

A. an array of individual test strips comprising at least two individual test strips arranged essentially parallel to one another within the test device, each of said test strip being characterized as comprising a porous medium having a linear fluid pathway and a test site defined as a delimited area of immobilized test kit reagent along said linear fluid pathway of said test strip; and B. a sample receiving web having at least two segments in fluid communication with each other and a common fluid application site, said sample receiving web being further characterized as having a sample application site, a base segment and at least one branched segment radiating from said base, wherein each of said base and said branched segment are in fluid communication (a) with each other at said sample application site and (b) with each of said test strips at two spaced apart areas on said test strip, for essentially coincident distributive flow of sample from said fluid application site onto each of said two spaced apart areas of said individual test strip within said test strip array, whereby, sample applied to said sample application site on said base segment effects distribution of an aliquot of sample to each of two spaced apart areas on said test strip and thereby essentially concurrent interaction of said sample with each of said test sites of said test strips within said test strip array.

2. The improved test device of claim 1, wherein each of the test strips of said test device comprises test kit reagents specific for (a) detection of an analyte of interest thereby providing for qualitative analysis thereof, (b) detection of the an analyte over a threshold or basal amount, thereby providing for measurement of an elevated level thereof or (c) detection of an analyte of interest over a range of concentration, thereby providing for semi-quantitative, analysis thereof.

3. The improved test device of claim 1, wherein said device comprises a housing having at least two components, which when assembled, define a chamber for containment and orientation of said sample receiving web and a plurality of test strips specific for detection of analytes(s) of interest, said housing being further characterized as having a face plate with a series of viewing windows corresponding with a test site of each of said test strip so as to permit observation of said test site under assay conditions and thereby the detection of any perceptible changes at said test site under assay conditions.

4. The improved test device of claim 3, wherein face plate of the housing is further characterized by a graphic information for performance or interpretation of said test.

5. The improved test device of claim 3, wherein the face plate and/or said complimentary base member have molded contours for placement, isolation or retention of the sample receiving web and test strips so as to maintain their proper orientation relative to one another within the chamber defined by each of said components of said housing.

6. In a fluid transfer system for delivery of a liquid from a common fluid application site within a diagnostic test device to a plurality of test strips within said diagnostic test device, the improvement comprising:

A. providing a diagnostic test device having, (1). an array of individual test strips comprising at least two individual test strips arranged essentially parallel to one another within the test device, each of said test strip being characterized as comprising a porous medium having a linear fluid pathway and a test site defined as a delimited area of immobilized test kit reagent along said linear fluid pathway; and (2). a sample receiving web having at least two segments in fluid communication with each other, said sample receiving web being further characterized as having a base segment and at least one branched segment radiating from said base, wherein each of said base and said branched segment are in fluid communication (a) with each other at a sample application site on said base segment and (b) with each of said test strips at two spaced apart areas on said test strip, B. applying a volume of sample to said sample application site on said base segment so as to effect passive distribution of an aliquot of said sample to each of two spaced apart areas of said test strips within said test strip array of said diagnostic test device, and thereby essentially concurrent interaction of said sample with each of said test sites of said test strips within said test strip array.

7. The improved fluid transfer system of claim 6, wherein each of said segments of the sample receiving web have a combined fluid capacity sufficient for absorption and transport of an immunochromatographic effective amount of fluid sample to each of the individual test strips of the test strips.

8. The improved fluid transfer system of claim 6, wherein each of said segments of the sample receiving web have a fluid capacity sufficient for absorption and transport of effective amounts of fluid sample so as to effect a clean separation of free from bound materials at said test site.

9. The improved fluid transfer system of claim 6, wherein each of said base and said branched segments of the sample receiving web are at angle of at least about 45 degrees relative to one another.

10. The improved fluid transfer system of claim 6, wherein each of said base and said branched segments of the sample receiving web are of essentially the same material.

11. In a method for the concurrent manual performance a plurality of diagnostic tests upon a common fluid sample with in common diagnostic test device, the improvement comprising:

A. providing a diagnostic test device having,
   (1). an array of individual test strips comprising at least two individual test strips arranged essentially parallel to one another within the test device, each of said test strip being characterized as comprising a porous medium having a linear fluid pathway and a test site defined as a delimited area of immobilized test kit reagent along said linear fluid pathway of said test strip; and
   (2). a sample receiving web having at least two segments in fluid communication with each other, said sample receiving web being further characterized as having a base segment and at least one branched segment radiating from said base,
   wherein each of said base and said branched segment are in fluid communication (a) with each other at a sample application site on said base segment and (b) with each of said test strips at two spaced apart areas on said test strip,
B. applying a volume of sample to said sample application site so as to effect passive distribution of an aliquot of said sample to each of two spaced apart areas of said test strips within said diagnostic test device, and thereby essentially concurrent interaction of said sample with each of said test sites of said test strips within said test strip array.

12. The improved method of claim 11, wherein said array of test strips comprises a drug of abuse test panel of tests.

13. The improved method of claim 11, wherein said array of test strips comprises an infectious disease test panel of tests.

14. The improved method of claim 11, wherein said array of test strips comprises a childhood disease test panel of test.

15. The improved method of claim 11, wherein said array of test strips utilize a test protocol wherein the indicator comprises a particulate label.

16. The improved method of claim 11, wherein said array of test strips utilize a test protocol wherein the indicator comprises an enzyme.

17. The improved method of claim 11, wherein said array of test strips utilize a test protocol wherein the indicator comprises a flourophore.

18. The improved method of claim 11, wherein said array of test strips utilize a test protocol wherein the indicator comprises a chromophore.

19. The improved method of claim 11, wherein said array of test strips utilize a test protocol wherein the indicator comprises a radioactive label.

* * * * *